US009364357B2

(12) United States Patent
Costello

(10) Patent No.: US 9,364,357 B2
(45) Date of Patent: Jun. 14, 2016

(54) DELIVERY CATHETER INCLUDING COLLAPSIBLE SLEEVE AND METHOD OF OPERATING SAME

(71) Applicant: Cook Medical Technologies LLC, Bloomington, IN (US)

(72) Inventor: Kieran Costello, Cullenagh (IE)

(73) Assignee: Cook Medical Technologies LLC, Bloomington, IN (US)

( * ) Notice: Subject to any disclaimer, the term of this patent is extended or adjusted under 35 U.S.C. 154(b) by 230 days.

(21) Appl. No.: 14/157,861

(22) Filed: Jan. 17, 2014

(65) Prior Publication Data

US 2014/0336742 A1 Nov. 13, 2014

Related U.S. Application Data

(60) Provisional application No. 61/820,878, filed on May 8, 2013.

(51) Int. Cl.

| | |
|---|---|
| ***A61F 2/06*** | (2013.01) |
| ***A61F 2/962*** | (2013.01) |
| *A61F 2/95* | (2013.01) |

(52) U.S. Cl.

CPC ......... *A61F 2/962* (2013.01); *A61F 2002/9517* (2013.01)

(58) Field of Classification Search

CPC .... A61B 1/00151; A61B 1/233; A61B 1/273; A61B 1/31; A61B 2017/1205; A61B 2017/12022; A61F 2/95; A61F 2/962; A61F 2/966; A61F 2002/9517; A61F 2002/9522; A61F 2002/9528; A61F 2002/9534; A61F 2002/9665; A61M 25/0199; A61M 25/0122

See application file for complete search history.

(56) References Cited

U.S. PATENT DOCUMENTS

| | | | | |
|---|---|---|---|---|
| 4,615,331 | A * | 10/1986 | Kramann ........... | A61B 1/00151 600/114 |
| 5,203,774 | A | 4/1993 | Gilson et al. | |
| 5,234,411 | A * | 8/1993 | Vaillancourt ..... | A61M 25/0111 604/158 |
| 5,334,160 | A | 8/1994 | Ellis | |
| 5,545,169 | A * | 8/1996 | Yarger ............ | A61B 17/00234 606/108 |
| 5,836,306 | A | 11/1998 | Duane et al. | |
| 8,114,057 | B2 | 2/2012 | Gerdts et al. | |
| 8,216,295 | B2 | 7/2012 | Benjamin et al. | |
| 2001/0044595 | A1* | 11/2001 | Reydel et al. ............ | A61F 2/95 604/98.02 |
| 2005/0240254 | A1 | 10/2005 | Austin | |
| 2005/0256373 | A1* | 11/2005 | Bar-Or .............. | A61B 1/00135 600/114 |
| 2005/0283223 | A1* | 12/2005 | Greenan .................. | A61F 2/95 623/1.11 |
| 2006/0025844 | A1 | 2/2006 | Majercak et al. | |
| 2010/0312325 | A1 | 12/2010 | Dorn | |

* cited by examiner

*Primary Examiner* — David C Eastwood

(74) *Attorney, Agent, or Firm* — Liell & McNeil

(57) ABSTRACT

A catheter system includes an introducer sheath and a delivery catheter having an external surface. A sleeve connector is supported on and axially movable relative to the external surface of the delivery catheter. A collapsible sleeve has a first end attached to the external surface of the delivery catheter at a first attachment and a second end attached to the sleeve connector at a second attachment. The catheter system includes a medical device placement configuration in which the delivery catheter is received through the introducer sheath, the sleeve connector is removably attached to the introducer sheath, and the collapsible sleeve is positioned radially between the external surface of the delivery catheter and an internal surface of the introducer sheath.

17 Claims, 2 Drawing Sheets

DELIVERY CATHETER INCLUDING COLLAPSIBLE SLEEVE AND METHOD OF OPERATING SAME

TECHNICAL FIELD

The present disclosure relates generally to a delivery catheter including a collapsible sleeve for use with an introducer sheath, and more particularly to a delivery catheter including a collapsible sleeve interconnecting an external surface of the delivery catheter and a sleeve connector that is supported on and axially movable relative to the external surface of the delivery catheter.

BACKGROUND

Introducers, or introducer sheaths, are used for minimally invasive placement of medical devices, such as catheters, into the vasculature. Introducers typically include a tube that is inserted percutaneously into a vascular structure and a valve, including a sealing member, positioned at a proximal end of the tube. The valve, which is positioned outside the body of the patient, may be a hemostasis valve for reducing blood loss at the valve. Delivery catheters are used for a variety of diagnostic and/or therapeutic purposes and may be introduced into the vascular structure through the hemostatic valve of the introducer. The introducer thus provides access for a delivery catheter, or other similar medical device, and protects walls of the vascular structure from damage during insertion of the delivery catheter.

According to some percutaneous vascular procedures, the delivery catheter may require repositioning, including insertion and withdrawal, relative to the introducer. For example, during a medical device placement procedure, a portion of the delivery catheter may require retraction relative to the introducer, to deploy the medical device. During this proximal retraction, or withdrawal, it may be necessary to maintain a stationary position of both another portion of the delivery catheter and the introducer, particularly in light of the friction between the sealing member of the valve and the delivery catheter. This maneuvering can be difficult, particularly since precise positioning and movement of the respective components is important for proper medical device placement.

U.S. Pat. No. 8,114,057 to Gerdts et al. (hereinafter “Gerdts”) discloses a stent delivery system including an adaptor having a valve, a coaxial catheter assembly configured to extend through the valve, and a telescoping sleeve including a plurality of telescoping tubes. The first tube of the plurality of telescoping tubes may be secured to the adapter using the valve and, when the coaxial catheter assembly is positioned through the adaptor, the first tube may be positioned between the catheter assembly and the adaptor. The telescoping sleeve may be proximally extended to abut a distal portion of a handle of the catheter assembly. As such, the portion of the catheter assembly between the adaptor and the handle may be inhibited from bowing or arching outward using the extended telescoping sleeves. In addition, the friction between the tubes of the telescoping sleeve may help inhibit the handle from moving distally relative to the adaptor during stent deployment using the coaxial catheter. Although the system of Gerdts may be useful for some applications, it should be appreciated that there is a continuing need for efficient and effective catheter systems.

The present disclosure is directed toward one or more of the problems or issues set forth above.

SUMMARY OF THE DISCLOSURE

In one aspect, a catheter system includes an introducer sheath and a delivery catheter having an external surface. A sleeve connector is supported on and axially movable relative to the external surface of the delivery catheter. A collapsible sleeve has a first end attached to the external surface of the delivery catheter at a first attachment and a second end attached to the sleeve connector at a second attachment. The catheter system includes a medical device placement configuration in which the delivery catheter is received through the introducer sheath, the sleeve connector is removably attached to the introducer sheath, and the collapsible sleeve is positioned radially between the external surface of the delivery catheter and an internal surface of the introducer sheath.

In another aspect, a catheter assembly includes a retractable sheath having an external surface and a catheter positioned inside the retractable sheath. A medical device is compressed between an outer surface of the catheter and an inner surface of the retractable sheath. A sleeve connector is supported on and axially movable relative to the external surface of the retractable sheath. A collapsible sleeve has a first end attached to the external surface of the retractable sheath at a first attachment and a second end attached to the sleeve connector at a second attachment. An outer section of the collapsible sleeve is folded over onto an inner section of the collapsible sleeve at a rolling fold.

In yet another aspect, a method of operating a catheter system is provided. The catheter system includes an introducer sheath and a delivery catheter having an external surface. The catheter system also includes a sleeve connector supported on and axially movable relative to the external surface of the delivery catheter, and a collapsible sleeve having a first end attached to the external surface of the delivery catheter at a first attachment and a second end attached to the sleeve connector at a second attachment. An outer section of the collapsible sleeve is folded over onto an inner section of the collapsible sleeve at a rolling fold. The method includes steps of inserting a distal portion of the delivery catheter through the introducer sheath, and removably attaching the sleeve connector to the introducer sheath to define a medical device placement configuration. According to the medical device placement configuration, the second attachment is positioned axially between the first attachment and the rolling fold, and a portion of the collapsible sleeve is positioned radially between the outer surface of the delivery catheter and an internal surface of the introducer sheath. The method also includes a step of proximally retracting at least a portion of the delivery catheter relative to the introducer sheath. The proximally retracting step includes proximally moving the rolling fold.

DETAILED DESCRIPTION

Figure 1:
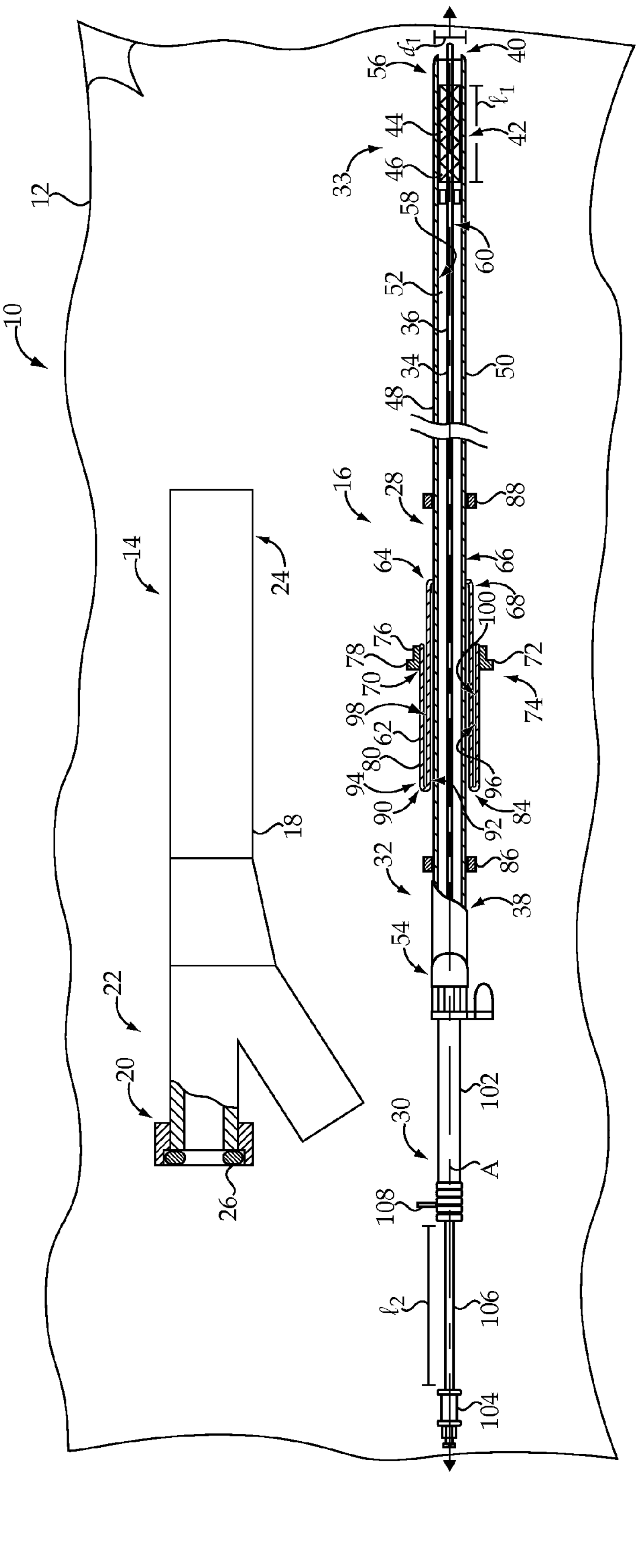
FIG. 1 is a partially sectioned side diagrammatic view of a catheter system, according to one embodiment of the present disclosure.

Referring to FIG. 1, there is shown a catheter system 10 according to one embodiment of the present disclosure. The catheter system 10 may include a number of components, which may be provided within a sterile, tear open package 12, as is known in the art. In performing a medical device deployment procedure on a patient, the components of the catheter system 10 and additional components may be used, depending upon the specifics of the procedure to be performed. As should be appreciated, however, components of the catheter system 10 might be separately packaged and/or the catheter system 10 might also include components in addition to those shown, including components routinely used in percutaneous vascular procedures.

In general, the catheter system 10 includes an introducer sheath 14 and a catheter assembly 16. Introducer sheaths, such as introducer sheath 14, are known and may be used to provide venous access in certain medical procedures, such as, a medical device deployment procedure. For example, an introducer needle may be inserted to access a vascular structure and then a wire guide may be threaded into the vascular structure through the introducer needle. The introducer sheath 14 may then be advanced over the wire guide to provided venous access for advancing various medical devices, such as, for example, the catheter assembly 16.

The introducer sheath 14, as shown, may have a tubular body 18 and may include a valve 20, such as, for example, a hemostasis valve, positioned at a proximal end 22 of the introducer sheath 14. During a percutaneous vascular procedure, the proximal end 22 of the introducer sheath 14 may remain outside a patient's body, while an open distal end 24 of the introducer sheath 14 may extend into the patient's body. Although a particular embodiment is shown, it should be appreciated that the introducer sheath 14 may vary in size, shape, and/or configuration, depending on the particular application. According to the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The valve 20, which may be attached to the introducer sheath 14 using any known attachment means, may be configured to minimize fluid loss during a procedure, and may include any known sealing member 26 for sealing against devices or wires inserted through the introducer sheath 14. For example, the valve 20 may be a hemostasis valve configured to seal around the catheter assembly 16 as the catheter assembly 16 is inserted through the introducer sheath 14 during a medical device deployment procedure to reduce blood loss during the procedure. Although a simplified valve 20 is shown, it should be appreciated that the introducer sheath 14 may include any type of hemostasis valve, or another type of valve, as an integral feature or a separate component, which may vary in complexity. For example, the valve 20, according to some embodiments, may be adjustable to selectively seal around medical devices inserted through the valve 20.

The catheter assembly 16 includes a delivery catheter 28 and a handle assembly 30, which may include relatively rigid components made from medical grade materials, disposed at a proximal end 32 of the delivery catheter 28. The delivery catheter 28, which also has a distal portion 33, may be a coaxial delivery device and may include a catheter, or inner shaft, 34 having an elongate body 36, a proximal end 38, a distal end 40, and a medical device support region 42 at the distal end 40 of the elongate body 36. According to some embodiments, the catheter 34, which may include a hollow tubular body defining a lumen, may range in length from several inches to several feet long, and may have a catheter wall diameter that is orders of magnitude smaller than its length. The elongate body 36 may be made from any common medical tube material, such as, for example, a plastic, rubber, silicone, or Teflon material, and may exhibit both firmness and flexibility.

A medical device 44 may be positioned over the catheter 34 at the medical device support region 42. According to the exemplary embodiment, the medical device 44 may include a radially expanding stent 46 for providing tubular support within a blood vessel, canal, duct, or other bodily passageway. Radially expandable stents, such as radially expanding stent 46, are known and may be expanded using a balloon, or other known device, positioned at a distal portion of a delivery device, such as catheter 34. Alternatively, and according to the exemplary embodiment, the radially expanding stent 46 may be made from a resilient or shape memory material, such as, for example, nitinol, that is capable of self-expanding from a compressed state to an expanded state without the application of a radial force on the stent 46. Such a stent 46 may be referred to as a "self-expanding" stent 46. Although a self-expanding stent 46 will be discussed herein, those skilled in the art should appreciate that the medical device 44 may include alternative radially expandable prosthetic implants. For example, the medical device 44 may include a self-expanding, or otherwise expandable, stent graft or venous filter.

According to some embodiments, an axial length of the self-expanding stent 46, or medical device 44, may be greater than about 100 mm. According to some embodiments, the medical device 44 may have an axial length of between about 10 mm and 300 mm. More particularly, the medical device 44 may range from 20 mm in length to 200 mm in length. It should be appreciated that such dimensions are provided for exemplary purposes only, and a variety of medical devices, having various sizes and configurations, may be deployed using the catheter system 10 described herein. Further, the self-expanding stent 46 may include a specialized coating, as is known to those skilled in the art.

A retractable sheath 48 has an elongate tubular body 50 defining a lumen 52 extending from an open proximal end 54 to an open distal end 56. As shown, the catheter 34 is telescopically received within the retractable sheath 48. When the self-expanding stent 46, or other medical device, is loaded onto the catheter 34, the self-expanding stent 46 may be restricted from self-expansion using the elongate tubular sheath 48, which is slidably received over the elongate tubular body 36 of the catheter 34. According to this configuration, the retractable sheath 48 restricts radial expansion of the self-expanding stent 46 by contacting the stent 46 with an inner wall surface 58 defining the lumen 52 of the retractable sheath 48. In particular, the medical device 44 is compressed between an outer surface 60 of the catheter 34 and the inner surface 58 of the retractable sheath 48. According to some embodiments, a ratio of a length $l_1$ of the medical device 44 to an outer diameter $d_1$ of the retractable sheath 48 is greater than fifty.

The catheter assembly 16 also includes a collapsible sleeve 62 having a first end 64 attached to an external surface 66 of the delivery catheter 28 or, more specifically, the retractable sheath 34 at a first attachment 68, and a second end 70 attached to a sleeve connector 72, which may be made from plastic or metal, at a second attachment 74. The collapsible sleeve 62 may be made from a flexible film, such as, for example, a medical grade polyethylene film, and may be positioned over a segment of the external surface 66 of the delivery catheter 28. The sleeve connector 72 may be supported on and axially movable relative to the external surface 66 of the delivery catheter 28 and, as shown, may include a tubular body 76 with a flange 78 extending radially therefrom.

The sleeve connector 72 may be slidable over at least a portion of the collapsible sleeve 62 along a longitudinal axis A of the delivery catheter 28.

As used herein, a "collapsible sleeve," such as sleeve 62, is a sleeve of material capable of being folded over onto itself. In particular, an outer section 80 of the collapsible sleeve 62 is folded over onto an inner section 82 of the collapsible sleeve 62 at a rolling fold 84. As shown, the sleeve connector 72 may be positioned over the inner section 82 of the collapsible sleeve 62, and as the sleeve connector 72 is moved proximally or distally along the delivery catheter 28 the rolling fold 84 is similarly displaced. For example, if the sleeve connector 72 is moved proximally along the delivery catheter 28, the outer section 80 may shorten, the inner section 82 may lengthen, and the rolling fold 84 may have a more proximal position relative to the delivery catheter 28. If the sleeve connector 72 is moved distally along the delivery catheter 28, the outer section 80 may lengthen, the inner section 82 may shorten, and the rolling fold 84 may have a more distal position relative to the delivery catheter 28. As used herein, a "rolling fold," such as fold 84, is a crease or fold along which a sleeve, such as the collapsible sleeve 62, is folded that is capable of being repositioned as opposing ends 64 and 70 of the collapsible sleeve 62 are moved closer together or farther apart.

First and second end stops 86 and 88 may be supported on the external surface 66 of the delivery catheter 28 and may be configured to restrict axial movement of the sleeve connector 72 therebetween. The end stops 86 and 88 may be useful to limit proximal and distal movement of the sleeve connector 72 before or during use of the catheter assembly 16 in a medical device deployment procedure, as will be described below. During manufacture, the collapsible sleeve 62 may be attached to the retractable sheath 48 using any known attachment means, including the use of mechanical and/or chemical bonding. According to some examples, the first attachment 68 may be formed using adhesives, heat welding, ultrasonic means, or the like. The second attachment 74 may be similarly formed, using any known attachment means. Further, the second attachment 74 may be formed by securing the collapsible sleeve 62 between multiple components of the sleeve connector 72.

A first side 90 of the collapsible sleeve 62 defined by an inner surface 92 of the inner section 82 and an outer surface 94 of the outer section 80 may have a greater coefficient of friction than a second side 96 of the collapsible sleeve 62 defined by an outer surface 98 of the inner section 82 and an inner surface 100 of the outer section 80. For example, it may be desirable to permit contacting surfaces of the collapsible sleeve 82 to slide easily relative to one another, while having increased friction between the collapsible sleeve 82 and the external surface 66 of the delivery catheter 28. The "attachments," as used herein, may refer to attachments of open ends 64 and 70 of the collapsible sleeve 62 that may facilitate a sealed environment within the collapsible sleeve 62, as will be described below.

To facilitate movement of the catheter assembly 16 during a medical device placement procedure, a clinician may manipulate the handle assembly 30 introduced above. For example, the handle assembly 30 may include a handle 102 attached to the proximal end 54 of the retractable sheath 48, and a hub 104 and cannula 106 operatively coupled to the proximal end 38 of the catheter 34. The hub 104 is located a deployment distance $l_2$ proximal of the handle 102 in a pre-deployment configuration, as shown in FIG. 1, with the deployment distance $l_2$ being greater than the length $l_1$ of the medical device 44. To deploy the medical device 44, and with a locking pin 108 removed, the clinician may maintain a stationary position of the hub 104, while proximally retracting the handle 102 along the cannula 106. As will be described below in the context of a medical device deployment procedure, the handle 102 is moved toward, and eventually contacts, the hub 104.

INDUSTRIAL APPLICABILITY

Figure 2:
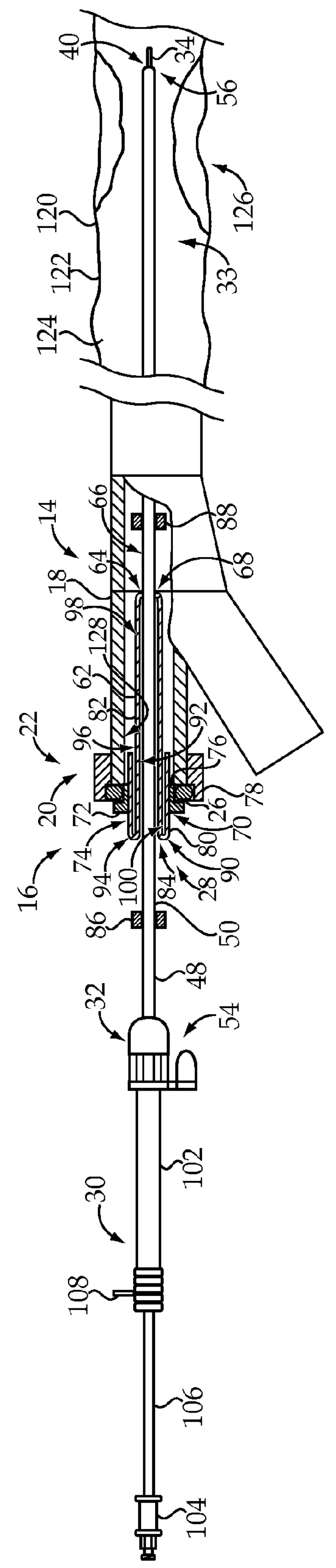
FIG. 2 is a partially sectioned side diagrammatic view of the catheter system of FIG. 1, shown in a medical device placement configuration.

Turning now to FIG. 2, a percutaneous vascular procedure using the catheter system 10 of FIG. 1 will be discussed with reference to a vascular structure 120 of a patient. The vascular structure 120, as should be appreciated, may include a vessel wall 122 defining a lumen 124 and may have a region of partial blockage 126. A clinician may first use an introducer needle and wire guide to gain access to the vascular structure 120 and position the introducer sheath 14 in a known manner. As shown in FIG. 2, the distal portion 33 of the delivery catheter 28 may be inserted through the introducer sheath 14, and valve 20 of the introducer sheath 14, and advanced toward a deployment location within the vascular structure 120 that corresponds to the region of partial blockage 126. Thus, the region of partial blockage 126 will also be referred to as the deployment location 126.

The sleeve connector 72 may then be removably attached to the introducer sheath 14, such as by using an interference fit or another known removable connection, to define a medical device placement configuration, as is shown in FIG. 2. For example, the tubular body 76 of the sleeve connector 72 may be received within the valve 20 and introducer sheath 14 and may be moved into sealing contact with the sealing member 26 of the valve 20. In particular, an outer diameter of the tubular body 76 of the sleeve connector 72 may be slightly smaller than an inner diameter of the valve 20 and/or introducer sheath 14 such that friction between the sleeve connector 72 and the sealing member 26, valve 20, and/or the introducer sheath 14 may create a sealing engagement and may form a removable attachment. Although an interference fit is described, it should be appreciated that alternative removable attachments are also contemplated.

According to the medical device placement configuration, the second attachment 74 is positioned axially between the first attachment 68 and the rolling fold 84, and a portion of the collapsible sleeve 62 is positioned radially between the external surface 66 of the delivery catheter 28 and an internal surface 128 of the introducer sheath 14. In fact, according to the exemplary embodiment, portions of both the inner section 80 and outer section 82 of the collapsible sleeve 62 may be positioned radially between the external surface 66 of the delivery catheter 28 and the sealing member 26. According to some embodiments, the tubular body 76 of the sleeve connector 72 and the inner and outer sections 80 and 82 of the collapsible sleeve 62 may all be positioned between the delivery catheter 28 and the sealing member 26. In addition, a fluid tight seal may be formed between the sleeve connector 72 and the external surface 66 of the delivery catheter 28 using the first attachment 68 and the second attachment 74.

Figure 3:
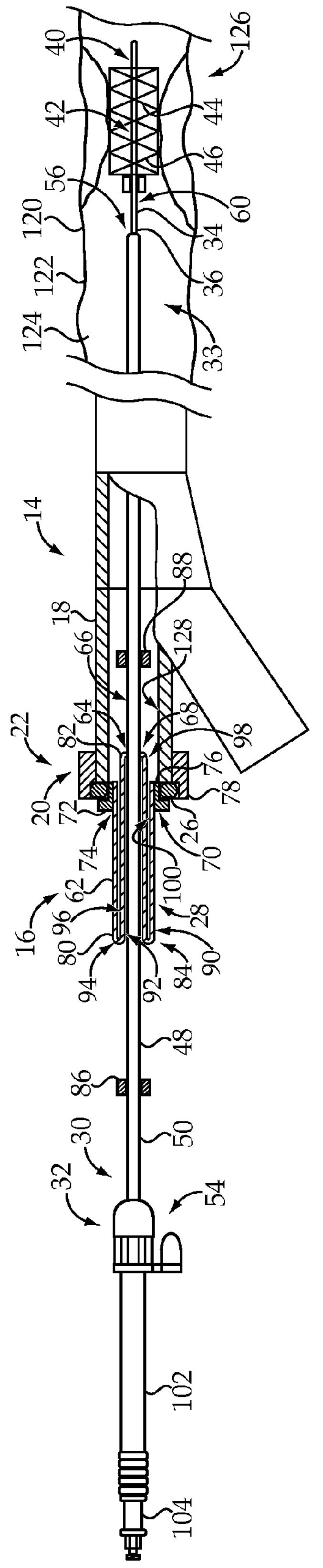
FIG. 3 is a partially sectioned side diagrammatic view of the catheter system of FIG. 1, shown in a medical device deployment configuration.

With the medical device 44 properly positioned at the deployment location 126, the medical device 44 may be deployed. In particular, the clinician may slide the retractable sheath 48 with respect to the catheter 34 while maintaining the catheter 34 stationary with respect to the deployment location 126. For example, to move the catheter system 10 into a medical device deployment configuration, which is shown in FIG. 3, the locking pin 108 may be removed and the clinician may maintain a stationary position of the hub 104, while proximally retracting the handle 102 along the cannula

106. The handle 102 is moved toward, and eventually contacts, the hub 104 in the medical device deployment configuration.

As the retractable sheath 48 is proximally retracted, the rolling fold 84 is moved proximally and the outer surface 98 of the inner section 82 of the collapsible sleeve 62 and the inner surface 100 of the outer section 80 are slid across one another in opposite directions. These contacting surfaces 98 and 100 may be made from or may include a surface layer having a low coefficient of friction to facilitate a reduced friction sliding. According to the medical device deployment configuration of FIG. 3, the delivery catheter 28 is received through the sealing member 26, the sleeve connector 72 is removably attached to the introducer sheath 14, and the rolling fold 84 has a position proximal to a previous position of the rolling fold 84 in the medical device placement configuration of FIG. 2.

With the retractable sheath 48 proximally retracted, as shown, the medical device 44, which may be a radially expanding stent 46, may be permitted to deploy at the deployment location 126, such as by expanding in a radial direction. It should be appreciated that the retractable sheath 48 is slid a deployment distance $l_2$ that is greater than a length $l_1$ of the medical device 44 to properly deploy the medical device 44.

The catheter system 10 described herein provides an effective and improved means for deploying medical devices, such as medical device 44, of various sizes and configurations, particularly when compared to conventional systems. In particular, the collapsible sleeve 62, including the rolling fold 84 and sliding surfaces 98 and 100, provides a means for retracting the retractable sheath 48 with respect to the introducer sheath 14 and valve 20 with reduced friction, as compared to conventional designs. As such, an easier and more precise medical device deployment may be achieved. In particular, the collapsible sleeve arrangement may reduce friction during sheath retraction that might otherwise remove or reposition the introducer sheath 14 and lead to reduced precision with respect to the deployment location 126. Since medical device deployment using a coaxial deployment device, as described herein, typically requires both hands of the clinician, a conventional procedure may require an additional person to hold stationary the introducer sheath 14 as the medical device 44 is deployed to reduce the inadvertent withdrawal of the introducer sheath 14. The procedure described herein, however, may not require such an additional person. As such, efficient and effective medical device deployment may be provided.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A catheter system, comprising:

an introducer sheath;

a delivery catheter having an external surface;

a sleeve connector supported on and axially movable relative to the external surface of the delivery catheter; and a collapsible sleeve having a first end attached to the external surface of the delivery catheter at a first attachment and a second end attached to the sleeve connector at a second attachment, and an outer section of the collapsible sleeve is folded over onto an inner section of the collapsible sleeve at a rolling fold;

wherein the catheter system includes a medical device placement configuration in which the delivery catheter is received through the introducer sheath, the sleeve connector is removably attached to the introducer sheath, and the collapsible sleeve is positioned radially between the external surface of the delivery catheter and an internal surface of the introducer sheath; and first and second end stops supported on the external surface of the delivery catheter and configured to restrict axial movement of the sleeve connector therebetween.

2. The catheter system of claim 1, wherein the introducer sheath includes a valve having a sealing member, and wherein, in the medical device placement configuration, the sleeve connector is in sealing contact with the sealing member.

3. The catheter system of claim 2, wherein a first side of the collapsible sleeve defined by an inner surface of the inner section and an outer surface of the outer section has a greater coefficient of friction than a second side of the collapsible sleeve defined by an outer surface of the inner section and an inner surface of the outer section.

4. The catheter system of claim 2, wherein the second attachment is positioned axially between the first attachment and the rolling fold.

5. The catheter system of claim 4, wherein the delivery catheter includes a retractable sheath and a catheter positioned inside the retractable sheath.

6. The catheter system of claim 5, further including a medical device compressed between an outer surface of the catheter and an inner surface of the retractable sheath.

7. The catheter system of claim 6, further including:

a handle attached to a proximal end of the retractable sheath; and a hub and cannula operatively coupled to a proximal end of the catheter;

wherein the hub is located a placement distance proximal of the handle in the medical device placement configuration, the placement distance is greater than a length of the medical device, and the hub contacts the handle in a medical device deployment configuration.

8. The catheter system of claim 7, wherein, in the medical device deployment configuration, the delivery catheter is received through the sealing member, the sleeve connector is removably attached to the introducer sheath, and the rolling fold has a position proximal to a previous position of the rolling fold in the medical device placement configuration.

9. A catheter assembly, comprising:

a retractable sheath having an external surface;

a catheter positioned inside the retractable sheath;

a medical device compressed between an outer surface of the catheter and an inner surface of the retractable sheath;

a sleeve connector supported on and axially movable relative to the external surface of the retractable sheath; and a collapsible sleeve having a first end attached to the external surface of the retractable sheath at a first attachment and a second end attached to the sleeve connector at a second attachment;

wherein an outer section of the collapsible sleeve is folded over onto an inner section of the collapsible sleeve at a rolling fold; and first and second end stops supported on the external surface of the retractable sheath and configured to restrict axial movement of the sleeve connector therebetween.

10. The catheter assembly of claim 9, wherein a first side of the collapsible sleeve defined by an inner surface of the inner section and an outer surface of the outer section has a greater coefficient of friction than a second side of the collapsible sleeve defined by an outer surface of the inner section and an inner surface of the outer section.

11. The catheter assembly of claim 9, further including:

a handle attached to a proximal end of the retractable sheath; and a hub and cannula operatively coupled to a proximal end of the catheter;

wherein the hub is located a placement distance proximal of the handle in a medical device placement configuration, the placement distance is greater than a length of the medical device, and the hub contacts the handle in a medical device deployment configuration.

12. The catheter assembly of claim 11, wherein the second attachment is positioned axially between the first attachment and the rolling fold in both the medical device placement configuration and the medical device deployment configuration.

13. The catheter assembly of claim 9, wherein the medical device is a self-expanding stent.

14. A method of operating a catheter system, the catheter system including an introducer sheath, a delivery catheter having an external surface, a sleeve connector supported on and axially movable relative to the external surface of the delivery catheter, and a collapsible sleeve having a first end attached to the external surface of the delivery catheter at a first attachment and a second end attached to the sleeve connector at a second attachment, wherein an outer section of the collapsible sleeve is folded over onto an inner section of the collapsible sleeve at a rolling fold, the method comprising steps of:

inserting a distal portion of the delivery catheter through the introducer sheath;

removably attaching the sleeve connector to the introducer sheath to define a medical device placement configuration in which the second attachment is positioned axially between the first attachment and the rolling fold, and a portion of the collapsible sleeve is positioned radially between the outer surface of the delivery catheter and an internal surface of the introducer sheath; and proximally retracting at least a portion of the delivery catheter relative to the introducer sheath;

wherein the proximally retracting step includes proximally moving the rolling fold.

15. The method of claim 14, wherein the removably attaching step includes moving the sleeve connector into sealing contact with a sealing member of a valve of the introducer sheath.

16. The method of claim 15, wherein the removably attaching step further includes forming a fluid tight seal between the sleeve connector and the external surface of the delivery catheter using the collapsible sleeve.

17. The method of claim 14, further including:

deploying a medical device at a deployment location after the inserting step and the removably attaching step;

wherein the deploying step includes proximally retracting a retractable sheath of the delivery catheter with respect to a catheter of the delivery catheter while maintaining the catheter stationary with respect to the deployment location, and proximally moving the rolling fold.

* * * * *